United States Patent [19]
Webster

[11] Patent Number: 5,410,406
[45] Date of Patent: Apr. 25, 1995

[54] METHOD AND APPARATUS FOR NONDESTRUCTIVE INSPECTION UTILIZING PHASE INTEGRATION AND RECORDING OF INDUCED VIBRATING NODAL PATTERNS

[75] Inventor: John M. Webster, Forest Hills, N.Y.

[73] Assignee: Holographics Inc., Long Island City, N.Y.

[21] Appl. No.: 11,991

[22] Filed: Feb. 1, 1993

[51] Int. Cl.⁶ .................... G01B 9/021; G01L 1/24
[52] U.S. Cl. .................... 356/347; 356/35.5
[58] Field of Search .................... 356/347, 35.5, 354, 356/300, 348; 359/10, 11; 73/655–657

[56] References Cited

U.S. PATENT DOCUMENTS

| | | | |
|---|---|---|---|
| 3,411,733 | 10/1975 | Bhuta et al. | 356/347 |
| 4,304,458 | 12/1981 | Huignard et al. | 356/347 |
| 4,408,881 | 10/1983 | Clarady, Jr. et al. | 356/347 |
| 4,871,255 | 10/1989 | Tenjinbayashi | 356/354 |
| 5,146,289 | 9/1992 | Newman | 356/35.5 |
| 5,227,982 | 7/1993 | Kipple et al. | 364/508 |

OTHER PUBLICATIONS

Birnbaum, G. and Vest, C. M., "Holographic Nondestructive Evaluation: Status and future", International Advances in Nondestructive Testing, 1983, vol. 9, pp. 257–282.

Fagot, H., Smigielski, P. Albe, F. and Arnaud, J., "Pulsed holographic Nondestructive testing on Aircraft", SPIE –The International Society for Optical Engineering, 1983, pp. 493–496.

Primary Examiner—Robert P. Limanek
Assistant Examiner—David B. Hardy
Attorney, Agent, or Firm—Brumbaugh, Graves, Donohue & Raymond

[57] ABSTRACT

A semi-monocoque structure is nondestructively tested by affixing an exciter to the outer skin of the structure for causing it to vibrate with an out-of-plane motion in a nodal pattern. Sensors either attached to or spaced from the outer surface provide signals representative of phase and acceleration information at likely anti-nodal points from which a computer-programmed controller senses resonant frequencies and amplitude of displacement. The controller automatically scans the excitation frequency through a predetermined range, and upon sensing a resonant frequency examines the signal to ascertain phase and amplitude of displacement of the anti-nodes and automatically adjusts their amplitude of displacement until the anti-nodes are optimized to be either bi-concave or concave/convex. When it has sensed optimum conditions, the controller twice triggers the Pockels cell of a double-pulse holographic camera at times of maximum plus and maximum minus displacement, respectively, whereby the resulting overlaid holograms are synchronized to points of maximum displacement of the anti-nodal pattern. It is from the fringe map of resulting interference patterns contouring the anti-nodal patterns that faults are interpreted.

16 Claims, 4 Drawing Sheets

METHOD AND APPARATUS FOR NONDESTRUCTIVE INSPECTION UTILIZING PHASE INTEGRATION AND RECORDING OF INDUCED VIBRATING NODAL PATTERNS

BACKGROUND OF THE INVENTION

This invention relates generally to non-destructive inspection of structures and, more particularly, to methods and apparatus for non-destructive inspection of monocoque and/or semi-monocoque structures which utilize excitation of nodal patterns in the skin of the structure and recording such patterns.

A semi-monocoque structure, such as an aircraft fuselage, is basically a skeleton over which a skin is secured, and may be characterized as a frame-lined shell. The skin, usually formed of metal which may vary in thickness or stiffness according to design requirements, is fixed to the skeletal framework so as to form a series of panels. It is from the skeletal framework surrounding each panel that the skin derives its strength. If the skin develops cracks, or is weakened or becomes detached from the skeletal framework, then a rupture can result causing impairment of the safety of the entire structure, particularly if the system is operated at pressure. Similarly, if the underlying structure cracks, or become seriously corroded, or the fastening system fails, structural failure can result. Since the semi-monocoque structure of an aircraft fuselage is usually pressurized, the fastening of the skin to the skeleton is critical, as is the integrity of the skeleton itself. Therefore, it is important that inspection techniques ascertain not only the condition of the skin and the fixers, such as rivets used to attach the skin to the framework, but also that of the underlying or sub-surface elemental skeleton.

However, it is very difficult to inspect the substructure of the skin of an aircraft fuselage for corrosion, broken fastenings, cracks or loose rivets, a situation referred to in the aircraft industry as "multi-element damage". Eddy current and acoustic systems heretofore used for the purpose achieve less than acceptable results. Visual inspection is a commonly used method, but substructural elements of a monocoque structure can be inspected with assurance only by using fiber-borescopes, or by stripping out interior instrumentation, linings or, in cases where a fault is suspected, making an X-ray examination, all of which procedures are time-consuming, expensive, and far from foolproof in their ability to detect faults.

Holographic interferometry has also been used to detect material flaws or nonhomogeneities through their effect on surface deformation when the test object responds to some mechanical or thermal load. By this technique complex laser light waves can be recorded and later reconstructed with such fidelity that they can be used to form interference fringe patterns. Using a pulsed laser, operated in a manner to produce two sequentially timed pulses and two holographic records—one of the light of the first pulse scattered by an object in some initial or known state and the other of the light from the second pulse scattered by the same object while it is subjected to vibration, for example—an image of the object with superimposed interference fringes is formed. These fringes are contour curves of constant surface displacement and provide a display of the deformation of the test object in response to the applied load. As this deformation may be affected by the presence of surface cracks or sub-surface defects, by comparing the fringe patterns for a flawed test object with those for a defect-free object it is possible to detect the presence of a subsurface defect, and possibly to estimate its size and depth.

It is also known that debonds and delaminations can be detected by inducing resonance of the locally flexible region created by the flaw. By using real-time holographic interferometry the surface response can be observed as the transducer which drives the vibration is tuned through a range of frequencies. This is accomplished by observing the vibrating object through a hologram which previously was recorded while the object was stationary. Vibrational techniques have been used to detect flaws in a variety of laminates and honeycomb materials as well as structures and components including airframe panels, turbine blades, helicopter rotors, cathode ray tube face plates and brake disks.

Interpretation of the fringe map of contour patterns is usually qualitative, consisting of searching for abrupt changes of curvature near cracks or for closely spaced "bull's eye" fringes near debonds, or fringes in normally fringe-free areas of low fringe count such as stringer or frame lines; this usually requires some operator judgment.

While the basic principles and techniques of holographic nondestructive evaluation are well-developed, to applicant's knowledge holographic NDE has not been satisfactorily utilized for the reliable detection of flaws in the substructure of monocoque or semi-monocoque structures. Accordingly, a need exists for apparatus and methods for nondestructively inspecting for multi-element damage in monocoque or semi-monocoque structures, such as aircraft fuselages.

The present invention utilizes a vibrational nondestructive technique for locating damage and flaws in such structures. Applicant's studies have shown that a semi-monocoque structure, when excited by a low energy vibrator attached to the skin, may freely vibrate at a number of resonant frequencies which have very narrow bandwidths, on the order of two or three cycles, compared to the separation of the frequencies. The panels circumscribed by the skeletal substructure resonate in a uniquely characteristic pattern of nodes and anti-nodes, and if the frequency of excitation, or the structural support of a panel is changed, then the nodal pattern changes shape, frequently becoming asymmetric, or in the extreme, changing frequency. The nodal patterns differ markedly in dependence on whether the excitation is applied at a node or is applied at an anti-node, for a particular frequency of excitation. In order for the panel to take up its own natural resonance and nodal pattern shape in a steady and constant manner, excitation must be applied at an anti-node.

A recording of changes in the nodal pattern can nondestructively reveal hidden flaws in the substructure and/or in the skin of the structure. However, applicant has recognized from results of his described studies that a recording of nodal pattern changes can reveal flaws with acceptable accuracy only if the recording is made at the instant certain conditions are present in the nodal pattern; these conditions are maximum displacement of the anti-nodes and satisfaction of certain conditions of phase of the anti-nodes and correct excitation.

Accordingly, a general object of the invention is to improve the accuracy of holographic nondestructive inspection methods and apparatus using vibrational techniques for the detection of flaws in monocoque and semi-monocoque structures.

A more specific object of the invention is to provide a method and apparatus for recording two time-displaced overlaying holograms of the vibrating skin of a monocoque structure at such times that the interference pattern generated by reconstruction of the holograms will optimally reveal flaws in the structure.

Another object is to provide a method and apparatus for correlating phase and amplitude of anti-nodal information in a vibrating structure to diagnose the structural condition of a monocoque structure.

SUMMARY OF THE INVENTION

Briefly, the nondestructive inspection method according to the invention includes the steps of mechanically exciting a vibrating nodal pattern in the outer skin of a monocoque structure, panels of which may freely vibrate at one or more resonant frequencies, scanning the frequency of excitation through a predetermined spectrum of frequencies which encompasses such resonant frequencies, and locking onto a resonant frequency which is uniquely characteristic of a certain phase relationship of the anti-nodes of the nodal pattern, varying the amplitude of excitation of the structure until the anti-nodes of the nodal pattern are optimized to be either bi-concave or concave/convex, and when such optimization occurs, recording two time-displaced overlaying holograms of the vibrating outer skin in synchronism with maximum plus and minus displacement, respectively, of an anti-node.

To carry out the method, an exciter, such a low energy vibrator, is affixed to the object surface for causing the object to vibrate with an out-of-plane motion in a nodal pattern. The exciter is attached to the skin at a likely anti-nodal point, and at least two sensors for measuring out-of-plane displacement are either attached to the surface at likely anti-nodal points or arranged such that they read out-of-plane surface displacement. The sensors provide a computer-programmed controller with anti-nodal and acceleration information from which resonant frequencies can be detected and amplitude of displacement derived for a given condition.

A scanner controlled by the controller automatically scans the excitation frequency of the vibrator through a predetermined range of frequencies at a preset rate. Upon sensing a resonant frequency, which it derives from accelerometer signals of predetermined amplitude, the programmed controller examines this signal to ascertain phase, amplitude of displacement and may refer to stored library information for comparing it with characteristics of known or expected resonant frequencies. The controller automatically adjusts amplitude of displacement of the anti-nodes to optimize fringe density in the final hologram.

If the sensed conditions satisfy conditions known to reveal in a hologram a structural fault in the object, then the controller locks onto the frequency, stores the information, and triggers the power pack for the laser of a double-pulse holographic camera at a point in time relative to the frequency and phase such that the laser amplifiers are at an optimum stage of excitation at times of maximum displacement of the anti-nodes. At this point, the Pockels cell is triggered twice, at times of maximum plus and minus displacement, whereby the resulting overlaying holograms are automatically synchronized to points of maximum displacement of the anti-nodal pattern. Interference patterns are generated at a separation of approximately one-half wavelength of light, contouring the anti-nodal patterns. It is from this fringe map of contour patterns, which is uniquely characteristic to any given structural condition, that faults are interpreted.

BRIEF DESCRIPTION OF THE DRAWINGS

Other objects, features and advantages of the invention will become apparent, and its construction and operation better understood, from the following detailed description when read in conjunction with the accompanying drawings, in which.

DESCRIPTION OF THE PREFERRED EMBODIMENT

Figure 1:
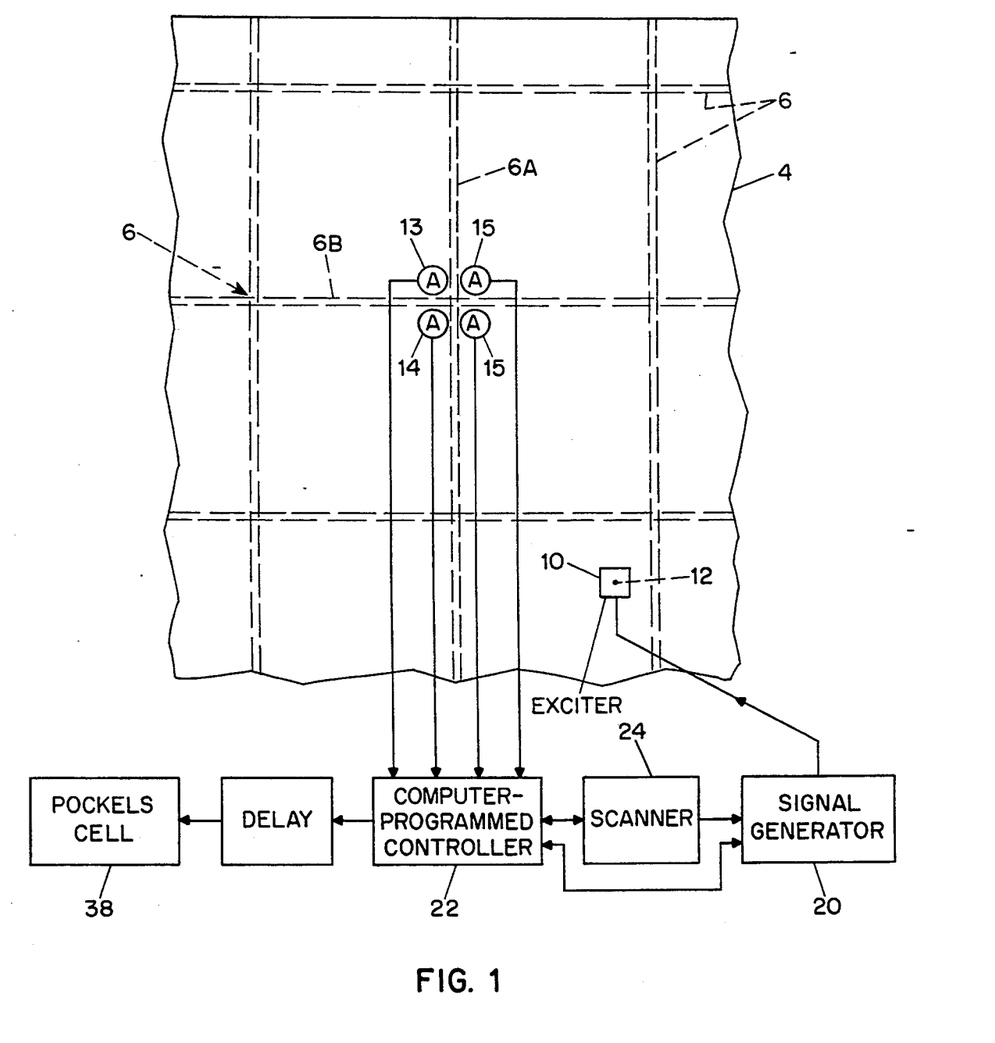
FIG. 1 is a fragmentary plan view of a semi-monocoque structure showing a simplified block diagram of a measuring system according to the invention.

Referring to FIG. 1, because of the nature of a semi-monocoque structure, viz, a thin skin 4, usually of metal, fastened to a framework of stringers 6, or frames or longerons, usually by rivets, it is possible to induce small amplitude vibrations in the skin, and also in the skeletal elements, with a low energy vibrator 10 attached to the skin. When subjected to such excitation, the skin surface will vibrate with an out-of-plane motion of a few microns displacement in a nodal pattern uniquely characteristic of its own structure and restraint and frequency of the excitation. Most structures have vibrational frequencies at which they exhibit a stable nodal pattern in which, for a given level of excitation, the amplitude of displacement is at a maximum; such preferred frequencies are known as resonances or resonant frequencies. Semi-monocoque structures may exhibit several resonant frequencies each of extremely narrow bandwidth; in the case of an aircraft fuselage for example, the bandwidth may be on the order of only one to three cycles at resonant frequencies in the range from one KHz to four KHz., or approximately 0.003%.

In semi-monocoque structures, like an aircraft fuselage, each panel, outlined by the underlying skeletal framework, although mechanically linked to the rest of the structure, can to some extent be considered as a separate structure when subjected to excitation at one of its resonant frequencies. A single panel, or more likely a section comprised of a number of similar panels, may all exhibit resonance at one particular frequency, while adjacent and slightly different panels do not respond in quite the same manner despite their being mechanically linked through the main structure. At some frequencies all of several similar contiguous panels may resonate over a very narrow bandwidth.

Furthermore, the structure must be correctly excited if a repeatable and stable nodal pattern is to be obtained. If, for example, the exciter is affixed to a panel at what would normally be a node (i.e., an area of no movement) the entire structure will be forced into an abnormal and unstable condition; this instability may, and usually does, extend beyond the panel to which the exciter is affixed and disturbs what would otherwise be normal nodal patterns on adjacent panels. Thus, a known condition can be achieved, or repeated, only if the structure is excited, with correct excitation, on an anti-nodal point.

Figure 2:
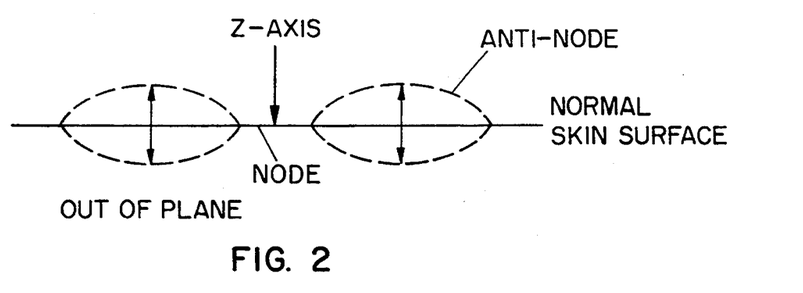
FIG. 2 is illustrates the phase relationship of out-of-plane motion of the skin surface of a sound mechanically excited monocoque structure.
Figure 3:
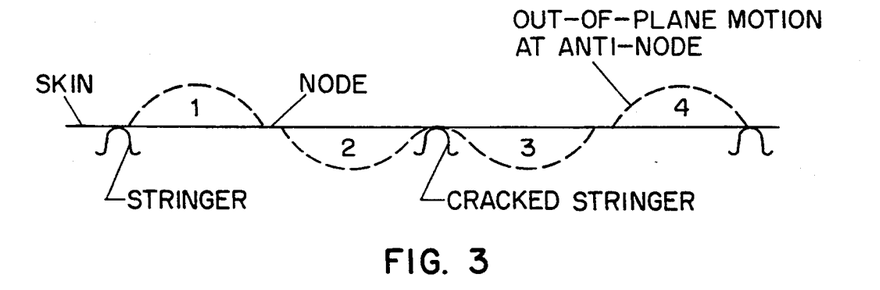
FIG. 3 shows a phase relationship of anti-nodes formed on the skin surface to either side of a stringer of a mechanically excited monocoque structure which may occur when the stringer is cracked.
Figure 4:
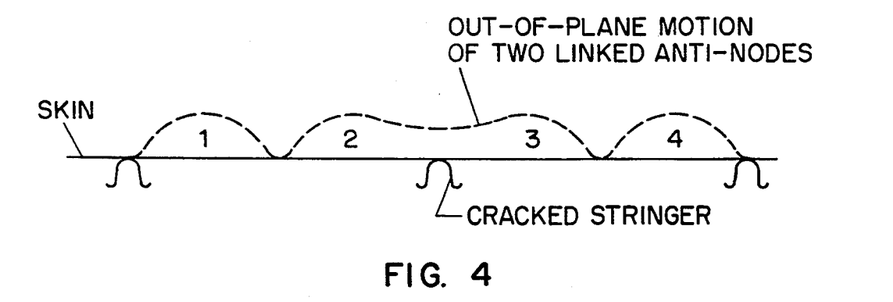
FIG. 4 shows two linked positive-going anti-nodes on the skin surface to either side of a stringer of a mechanically excited monocoque structure which occurs when the skin has become unfastened from the stringer.
Figure 5:
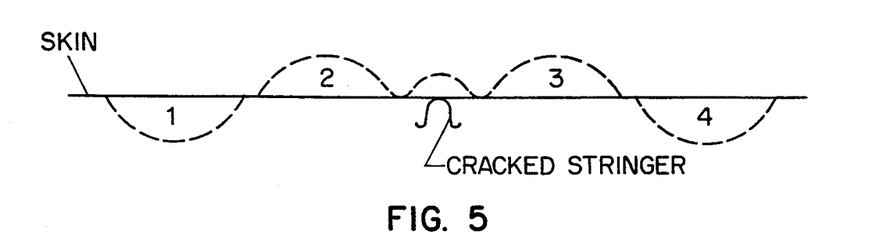
FIG. 5 shows positive-going anti-nodes on the skin surface to either side of, and also over, a stringer of a mechanically excited monocoque structure which may be formed when the stringer is cracked.

The nodal pattern adopted by any panel or array of contiguous panels will be dependent upon the size, shape and resonant frequency of the structure, but whatever the pattern may be in a sound (i.e., unflawed) structure it will be altered if the one or more of the structural elements underlying the skin is altered, as by fracture or becoming detached from the skin. Thus, while a sound structure of a given shape might exhibit, at a particular excitation frequency, the nodal pattern depicted in FIG. 2 having a node at the surface of the skin and out-of-phase anti-nodes to either side of the node, the pattern will change if say, a part of the supporting structure, for example, a stringer, were fractured or corroded, to one having an unsymmetrical appearance or exhibiting anti-node spreading across the fractured element. Applicant has discovered, however, that such departures from the normal fringe pattern of a sound structure can be reliably interpreted as a fault or flaw only if anti-nodes formed in the skin surface to either side of a suspect stringer (for example) satisfy certain phase conditions at the instant of recording. For example, a fractured stringer in the skeletal structure, whether fractured totally or only partially, will be manifested by a change in resonant frequency and resulting disturbance of the skin, which should be visible in a recording of the nodal pattern. However, if the nature of the flaw in the stringer is such that it no longer restrains the affected panel and/or panels next to it in its normal way the uniqueness of the skin disturbance may be lost, or the fault otherwise "masked". For example, applicant's studies have shown that when vibrations are induced in the skin of a semi-monocoque structure supported on three stringers as depicted in FIG. 3, wherein the intermediate stringer is cracked, and the anti-nodes to either side of the faulty stringer are in phase (as are anti-nodes 2 and 3) then the crack will be forced closed when both anti-nodes are concave (that is, the out-of-plane motion is inward from the normal skin surface) to cause the faulty stringer to appear to behave as a sound stringer and thus conceal the fault. Conversely, as depicted in FIG. 4, when two in-phase anti-nodes in the skin surface to either side of a cracked stringer are convex (that is, the out-of-plane motion is outward from the normal surface) the crack of a fracture is forced open and may form, instead of the two linked anti-nodes (2 and 3) depicted in FIG. 3, a convex anti-node directly over the cracked stringer which is in-phase with two in-phase convex anti-nodes to either side thereof, as shown at 2 and 3 in FIG. 5.

Figure 6:
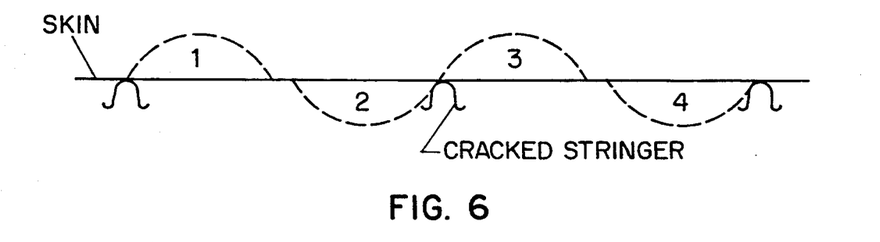
FIG. 6 shows another possible phase relationship of anti-nodes which may be formed on the skin surface to either side of a stringer of a mechanically excited monocoque structure when the stringer is cracked.

FIG. 6 depicts another possible phase condition of anti-nodes formed to either side of a cracked stringer; here the anti-nodes to either side of the fault are 180° out of phase, but the skin mobility caused by the crack in the frame or stringer (or by a loose rivet, as another example) will appear in the hologram as a linking together of interference fringes across the area of the fault. Accordingly, a fault which exhibits this nodal pattern will be revealed in recorded time-displaced holograms of the vibrating surface, if the anti-nodes are optimized to be either bi-concave or concave/convex.

Figure 7:
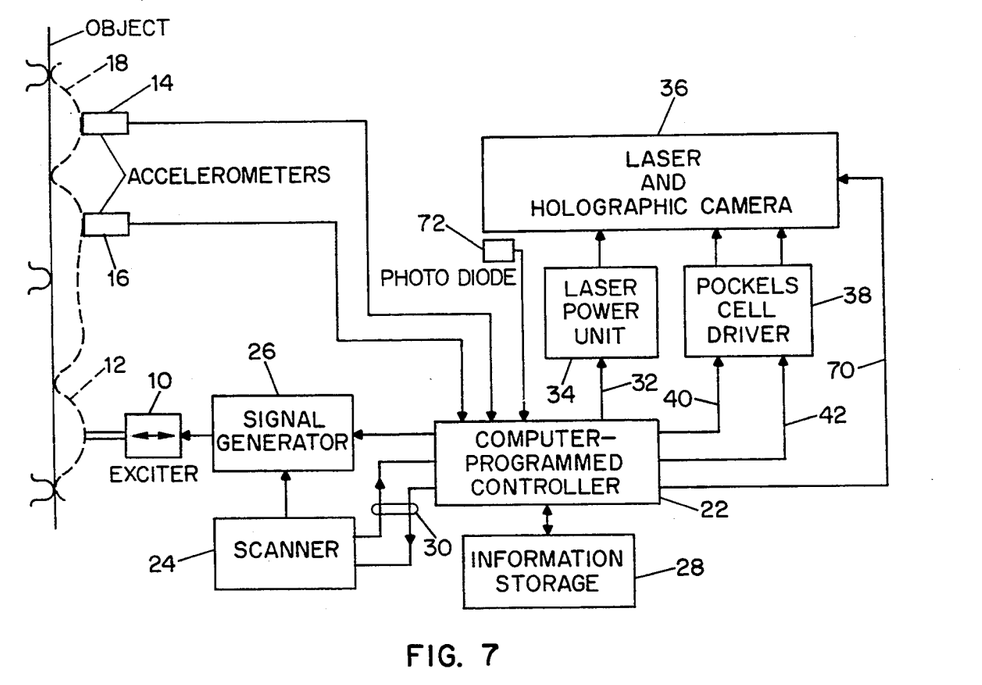
FIG. 7 is a block diagram of a control system according to the invention for controlling a double-pulse holographic camera.

FIG. 7 is a block diagram of a control system for adjusting the displacement of the anti-nodes of a nodal pattern formed on the surface of a vibrationally excited object to optimize fringe density in the final hologram, and for automatically recording two time-displaced holograms synchronized to the maximum points of displacement of the anti-nodal pattern. A portion of the control system is also shown in FIG. 1 with the object being inspected shown in elevation so as to depict the relative locations of two pairs of sensors. An exciter 10, such as a low energy vibrator, is affixed to the surface of the object being inspected, in this case a semi-monocoque structure having a thin skin secured to a framework of stringers, for causing the object to vibrate with an out-of-plane motion, taking-up a nodal pattern. Exciter 10 is attached at the approximate location of an anti-nodal point 12, and at least one pair, and preferably two pairs of sensors for measuring out-of-plane surface displacement are attached to the surface at likely anti-nodal points. As shown in plan in FIG. 1 and schematically in FIG. 7, sensors 14, 16 of a first pair are located in the general vicinity of adjacent corners of a first pair of contiguous panels at opposite sides of a stringer 6A being inspected, at which anti-nodes are likely to occur. If a second pair of sensors is used, the sensors 13, 15 of that pair are located in the vicinity of adjacent corners of a second pair of panels delineated from the first pair by a cross-stringer or frame 6B and at opposite sides of stringer 6A, at which anti-nodes are also likely to occur. The sensors may be any one of several available devices conventionally employed in NDI, such as accelerometers or piezoelectric cells which would be affixed to the skin-surface, or non-contacting sensors such as stationary or scanning laser Doppler anemometers, which measure the rate of change, and the direction, of displacement of the respective anti-nodes. These signals, which indicate whether an anti-node is positive or negative, that is, coming toward or going away from the viewer along the Z-axis, are applied as inputs to a computer-programmed controller 22 programmed to detect resonant frequencies and to determine amplitude of displacement of the observed anti-nodes for a given condition.

A scanner 24 controlled by controller 22 automatically scans the frequency of a signal generator 26 that drives exciter 10 at a predetermined rate, whereby to scan the frequency of the exciter through a predetermined range of frequencies which encompasses resonant frequencies likely to occur in the object being inspected. Upon sensing a resonant frequency, which is derived from accelerometer signals of predetermined amplitude, the controller examines this signal to ascertain phase and amplitude of displacement of the anti-nodes, and, if indicated, to compare the signal's characteristics with library information concerning known or expected resonant frequencies stored in an information storage device 28 coupled to the controller. The controller 22 automatically adjusts, via a control line 30, the amplitude of the signal outputted by signal generator 26, and consequently the power output of the exciter 10, to thereby adjust the amplitude of displacement of the anti-nodes to optimize fringe density in the final hologram.

When the controller determines that the characteristics of the anti-nodes it has sensed satisfy conditions known to reveal in a recorded hologram a structural fault in the object, then the controller locks onto the resonant frequency which resulted in such satisfaction, stores the frequency and displacement information in information storage device 28, and triggers, via a line 32, a power unit 34 for the laser of a double-pulse holographic camera, both represented by the block 36. Except for modifications to be described presently, the camera is of the type conventionally used as a diagnostic tool in nondestructive testing as a means of visualizing microscopic physical changes in the surface of an object. The laser preferably is a ruby laser because of the wavelength of its coherent light, for which photographic emulsion of high sensitivity and resolution are available, the good spatial and temporal coherence of the output beam, and its ability to generate two or more Q-switched pulses during one pump cycle. The requirement in double-pulse holography that the energy of the two pulses be equal can be achieved by adjusting the delay between the flashlamp trigger and the first Q-switch pulse, by adjusting the voltage of the Pockels cell, and by selecting the lamp input energy. By changing one or more of these parameters, one can obtain equal output energies in both pulses for pulse spacings falling in the range from say, one microsecond to one millisecond. In accordance with the present invention, the power unit is triggered at a point in time relative to the locked-on resonant frequency and phase that the laser amplifier is at an optimum stage of excitation during the interval between the times the anti-node exhibits maximum displacement in opposite directions. Out-of-plane displacement toward the accelerometers is hereafter referred to as "plus displacement" and displacement in the opposite direction, i.e., inwardly from the normal plane of the object surface, will be referred to as "minus displacement". At this point in time the Pockels cell is triggered twice by a Pockels cell driver 38, first via a line 40 in response to maximum plus displacement, and second via a line 42 in response to maximum minus displacement, whereby the resulting overlaying time-displaced holograms are automatically synchronized with times of maximum plus and minus displacement of the anti-nodal pattern.

It is essential to the analysis of the resulting hologram for perturbations of its fringe pattern from the norm that the human inspector, or automatic inspection or analyzing equipment, be informed of individual anti-nodal phases and relative phases; without such information, a fault could be masked. In conventional double-pulsed holography previously used for non-destructive testing, it has not been possible to derive this information directly from the hologram. It can be shown that if the reference beam of the holographic camera is tilted a few tens of milli-radians during the period between the two separated laser pulses, phase information can be easily derived from the resulting hologram. Characteristically, anti-nodes appear in a semi-symmetrical form similar to contour lines on a survey map. If the observation viewpoint is moved across the hologram, in the same direction that the reference beam was swept, these contour lines will appear to collapse inward or outward depending on their particular phase, viz: inward denoting "minus displacement" or a valley, and outward denoting "plus displacement" or a hill.

Figure 8:
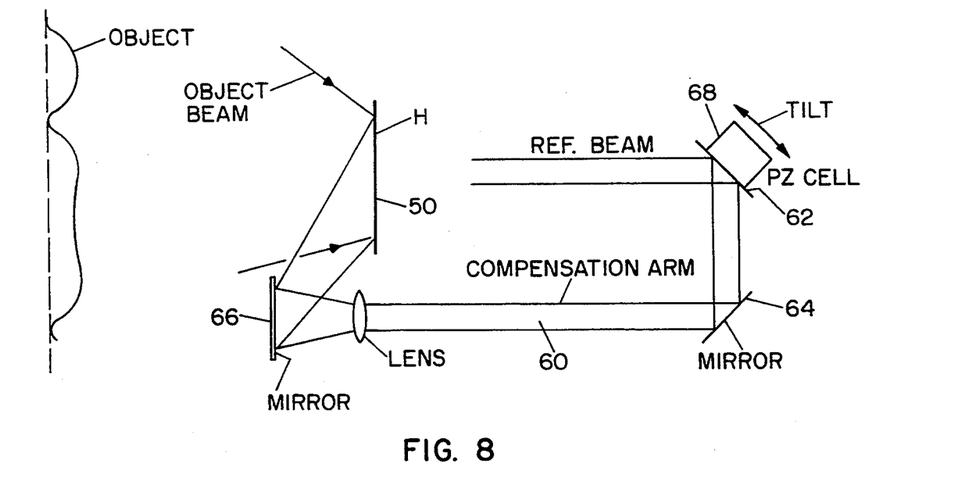
FIG. 8 is an optical schematic of a holographic camera.

In accordance with the invention, the reference beam is tilted between laser pulses by a mirror embodied in the double-pulse camera, a partial optical schematic of which is shown in FIG. 8. The camera reconstructs a hologram 50 from the object beam reflected from the object and a reference beam. Equalization of the path lengths of both the reference beam and the object beam is achieved by a compensation arm 60, which for compactness is folded via a plurality of mirrors 62, 64 and 66. One of the mirrors, mirror 62 in the illustration, is mounted on a piezoelectric cell 68 capable of tilting the incident reference beam through a small angle, much less than one degree, in response to an electrical signal generated by controller 22 and applied via line 70 (FIG. 7) within the period separating the two laser pulses. The mirror tilt may be vertical or horizontal. Devices other than a piezo-electric cell may be employed to tilt the beam, such as a solenoid-operated tilting mirror.

A photodiode 72 mounted in camera 36 within or in close proximity to the object beam provides a signal to controller 22 from which the controller determines the amplitude of the object beam arriving at the hologram. The controller also examines the quality of the two output pulses from the laser and provides information to an operator indicative of whether a hologram of good quality is likely to result.

Figure 9:
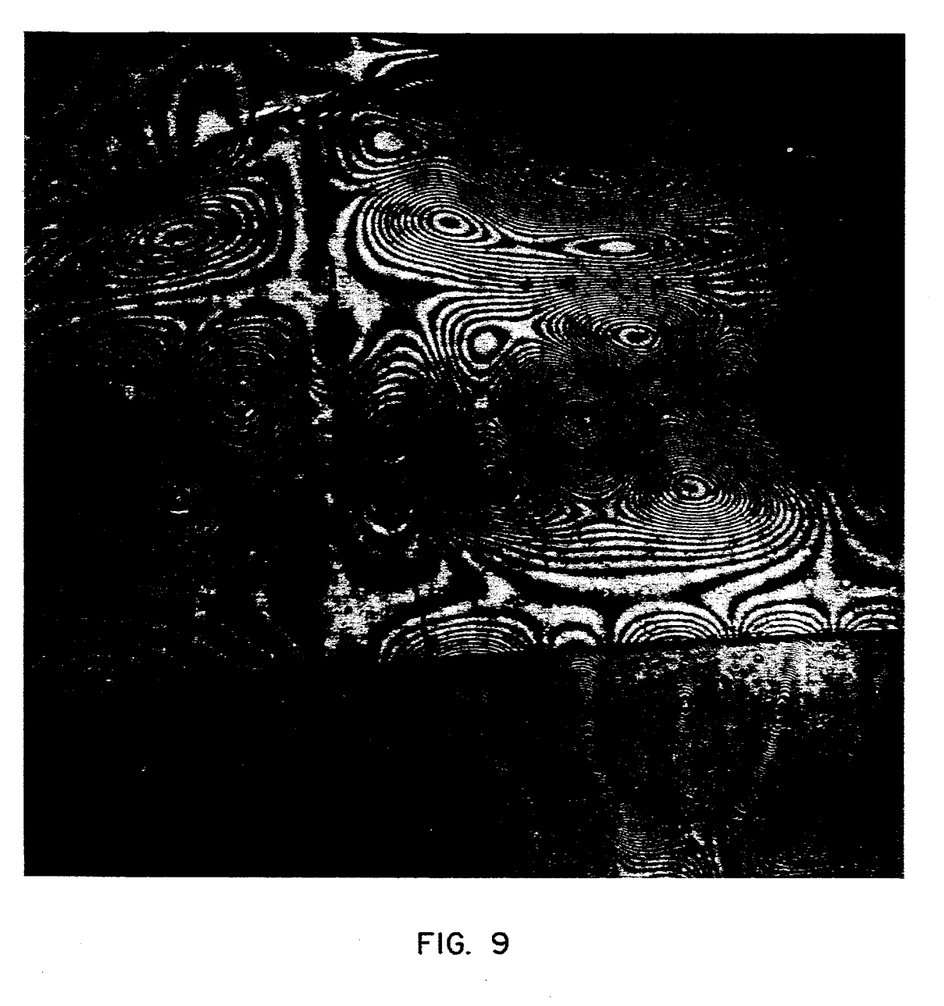
FIG. 9 is an interferogram which manifests the type of fault described in FIG. 4.

FIG. 9 is a photocopy of an interferogram, recorded in accordance with the described method, of several contiguous vibrating panels of the skin of an aircraft fuselage which are circumscribed by a substructure of interconnected stringers. In those panels circumscribed by sound stringers, the contour lines of the fringe patterns are generally confined within the panel boundaries. It will be seen from examination of a portion of the interferogram slightly to the left of the center that the contour lines representing a convex anti-node in the panel to the left of a generally vertical line, signifying a stringer, extend across that line and are connected to contour lines representing a convex anti-node in the panel to the right of the vertical line. These anti-nodes are in-phase and, additionally, a convex anti-node which is in-phase with the other two, occurs directly over the vertical line (i.e., the stringer of the semi-monocoque structure). As discussed earlier in connection with FIG. 4, this pattern of two convex in-phase anti-nodes to either side of a stringer, connected by a convex in-phase anti-node, is indicative of a cracked stringer in which the crack would not have been revealed except for it having been forced open by the anti-nodal pattern developed in the vicinity of the fault.

Although the invention has been described as applicable to the nondestructive inspection of semi-monocoque structures, it is apparent that the concepts disclosed herein are equally applicable in the inspection of objects of other forms. Also, while the invention has been described with a certain degree of particularity, it is to be understood that this disclosure has been made by way of example only and that numerous changes in the details of the apparatus may be made without departing from the spirit and scope of the invention.

I claim:

1. Method for nondestructively inspecting for faults in a semi-monocoque structure consisting of a skeletal framework of interconnected structural elements to which an outer skin is secured and wherein said framework divides the outer skin into a multiplicity of contiguous panels each of which will freely vibrate at one or more resonant frequencies when said outer skin is vibrationally excited at frequencies which respectively correspond to said one or more resonant frequencies in patterns of nodes and anti-nodes in which, in the absence of a fault in an underlying structural element under inspection, the nodes are located over, and the anti-nodes occur in pairs located on opposite sides of said structural element under inspection, which patterns change shape in response to the presence of a fault in the structural element under inspection and the frequency at which said outer skin is excited into resonance, comprising the steps of:

(a) mechanically exciting said outer skin of said structure over a predetermined spectrum of frequencies which encompasses said one or more resonant frequencies for causing said outer skin to vibrate at said one or more resonant frequencies in patterns of nodes and out-of-plane anti-nodes and locking onto that one of said one or more resonant frequencies which uniquely characterizes either a bi-concave or a concave/convex phase relationship between anti-nodes located to either side of said structural element under inspection, either of which phase relationships is indicative of a fault in said structural element under inspection;

(b) varying the amplitude of vibration at said locked on frequency until the out-of-plane displacement of said anti-nodes exhibiting either a bi-concave or a concave/convex phase relationship is optimized; and (c) synchronously with optimization of said out-of-plane displacement of said anti-nodes exhibiting either a bi-concave or a concave/convex relationship, recording time-displaced overlaying holograms of the vibrating outer skin of said structure for producing an interferogram of contour patterns which visually display the presence and location of faults.

2. The method as defined in claim 1, wherein said outer skin of said structure is mechanically excited by a vibrator affixed to said outer skin at a location thereon at which an anti-node can be expected to occur.

3. The method as defined in claim 2, wherein the method further comprises the step of integrating the relative phase, the out-of-plane displacement and the vibration frequency at which a pair of anti-nodes formed in the outer skin of said structure at opposite sides of a structural element under inspection exhibit a phase relationship which is either bi-concave or concave/convex.

4. The method as defined in claim 3, wherein said step of integrating includes the steps of:

scanning said frequency of excitation over said predetermined spectrum of frequencies, locking the excitation frequency onto that resonant frequency which uniquely characterizes a phase relationship between said pair of anti-nodes which is either bi-concave or concave/convex, while the excitation frequency is locked onto said that resonant frequency adjusting the amplitude of excitation until the anti-nodes of said pair exhibit maximum out-of-plane displacement.

5. The method as defined in claim 1, wherein the method further comprises the step of integrating the phase, the out-of-plane displacement and the vibration frequency at which said anti-nodes exhibit a phase relationship which is either bi-concave or concave/convex for determining when out-of-plane displacement thereof has been optimized.

6. The method as defined in claim 1, wherein said structure is mechanically excited by a vibrator affixed to a panel of said outer skin defined in part by a structural element of said framework under inspection at a location thereon at which an anti-node can be expected to occur, and wherein the method further comprises the step of integrating the phase and out-of-plane displacement of a pair of anti-nodes formed in respective panels of said outer skin at opposite sides of said structural element under inspection at an excitation frequency corresponding to that resonant frequency which maximizes out-of-plane displacement of said pair of anti-nodes for determining when said out-of-plane displacement has been optimized.

7. Apparatus for nondestructive inspection for faults in a semi-monocoque structure consisting of a skeletal substructure of interconnected structural elements to which an outer skin is secured and wherein said structural elements sub-divide the outer skin into a multiplicity of contiguous panels which will freely vibrate at one or more resonant frequencies when said outer skin is vibrationally excited at frequencies which respectively correspond to said one or more resonant frequencies in patterns of nodes and anti-nodes in which, in the absence of a fault in an underlying structural element under inspection, the nodes are located over, and the anti-nodes occur in pairs positionally located on opposite sides of said structural element under inspection, which patterns change shape in response to the presence of a fault in the underlying structural element under inspection and to the frequency at which said outer skin is excited into resonance, said apparatus comprising, in combination:

means adapted to be affixed to the outer skin of said structure at a location thereon at which an anti-node can be expected to occur and responsive to an excitation signal for mechanically inducing vibrations in the outer skin of said structure;

means for scanning the frequency of said excitation signal through a predetermined spectrum of frequencies which encompasses said one or more resonant frequencies for causing said outer skin to vibrate at said one or more resonant frequencies in patterns of nodes and out-of-plane anti-nodes having amplitude and a direction into or out from the plane of said outer skin and locking onto that excitation frequency which corresponds to that one of said one or more resonant frequencies which uniquely characterizes either a bi-concave or concave/convex phase relationship between anti-nodes of a pair located at opposite sides of an underlying structural element under inspection, either of which phase relationships element under inspection, either of which phase relationships is indicative of a fault in the underlying structural element under inspection;

means for sensing the amplitude and direction of out-of-plane displacement of the surface of said outer skin at each of first and second anti-nodes of a first pair located in first and second panels, respectively, of said outer skin at opposite sides of said underlying structural element under inspection;

means for integrating the sensed direction and out-of-plane displacement of said first and second anti-nodes of said first pair of anti-nodes over said predetermined spectrum of frequencies until that one of said resonant frequencies which uniquely characterizes either a bi-concave or concave/convex phase relationship between said first and second anti-nodes is reached and the out-of-plane displacement of said first and second anti-nodes is optimized; and means operative in response to and synchronously with the optimization of the out-of-plane displacement of said first and second anti-nodes of said first pair for recording two time-displaced holograms of that portion of the vibrating outer skin of said structure which overlies said structural element under inspection to produce an interferogram of contour patterns which visually displays the presence and location of a fault.

8. The apparatus defined in claim 7, wherein said means for recording comprises holographic camera means.

9. The apparatus defined in claim 7, wherein said means for mechanically inducing vibrations comprises an electro-mechanical vibrator driven by said excitation signal, means for varying the frequency of said excitation signal over said spectrum of frequencies, and means for adjusting the amplitude of said excitation signal to a value at which the out-of-plane displacement at each of said first and second anti-nodes of said first pair of anti-nodes is maximized.

10. The apparatus defined in claim 7, wherein said means for sensing amplitude and direction of out-of-plane displacement comprises first and second accelerometers of contacting type adapted to be affixed to said outer skin surface substantially at the locations of said first and second anti-nodes, respectively.

11. The apparatus defined in claim 7, wherein said means for sensing amplitude and direction of out-of-plane displacement comprises sensors of non-contacting type adapted to be arranged with respect to said outer skin surface so as to sense out-of-plane surface displacement at each of said first and second anti-nodes of said first pair.

12. The apparatus defined in claim 7, wherein said apparatus further comprises means for sensing the amplitude and direction of out-of-plane displacement of the surface of said outer skin at each of third and fourth anti-nodes of a second pair of anti-nodes located in third and fourth panels, respectively, of said outer skin which are disposed at opposite sides of said structural element under inspection and contiguous with said first and second panels, respectively.

13. The apparatus defined in claim 12, wherein said means for sensing the amplitude and out-of-plane displacement of the surface of said skin at said third and fourth anti-nodes of said second pair comprises third and fourth accelerometers of contacting type positioned substantially at said third and fourth anti-nodes, respectively, each for producing an output signal representative of the amplitude and direction of out-of-plane displacement of said outer skin at a respective anti-node.

14. The apparatus defined in claim 12, wherein said means for integrating comprises computer means connected to receive from said sensing means signals representative of the amplitude and direction of out-of-plane displacement of said outer skin at respective locations of said first, second, third and fourth anti-nodes and programmed to actuate said means for recording when the out-of-plane displacement of said outer skin at the locations of said first, second, third and fourth anti-nodes is optimal for said time-displaced holograms to reveal a fault, if present, in the structural element under inspection.

15. The apparatus defined in claim 7, wherein said means for integrating comprises computer means connected to receive from said sensing means signals representative of the amplitude and direction of out-of-plane displacement of the surface of said outer skin at said first and second anti-nodes and programmed to actuate said means for recording when the out-of-plane displacement of said first and second anti-nodes is optimal for said time-displaced holograms to reveal a fault, if present, in the structural element under inspection.

16. The apparatus defined in claim 15, wherein said means for mechanically inducing vibrations comprises a vibrator driven by said excitation signal, and wherein said computer means is programmed to vary the frequency of said excitation signal through said predetermined spectrum of frequencies and to lock onto a frequency which corresponds to that one of said one or more resonant frequencies at which the phase relationship between said first and second anti-nodes of said first pair is either bi-concave or concave/convex and then to adjust the amplitude of said excitation signal to a level at which the out-of-plane displacement of said outer skin at the locations of said first and second anti-nodes of said first pair is maximized.

* * * * *